US00PP09600P

United States Patent [19]

Weatherly

[11] Patent Number: Plant 9,600

[45] Date of Patent: Jul. 9, 1996

[54] FLORIBUNDA ROSE PLANT NAMED 'PROBERG'

[75] Inventor: Lilia M. Weatherly, Tasmania, Australia

[73] Assignee: Weeks Wholesale Rose Grower, Inc., Upland, Calif.

[21] Appl. No.: 511,956

[22] Filed: Aug. 7, 1995

[51] Int. Cl.[6] ..... A01H 5/00

[52] U.S. Cl. ..... Plt./22

[58] Field of Search ..... Plt./1, 22, 7.1

*Primary Examiner*—Howard J. Locker

*Attorney, Agent, or Firm*—Christie, Parker & Hale

[57] ABSTRACT

A new floribunda rose variety producing pink blush flowers.

1 Drawing Sheet

SUMMARY OF THE INVENTION

The present invention relates to a new and distinct variety of rose plant of the floribunda rose class, which was discovered as a mutation in a controlled planting of the variety known as 'Iceberg'. The varietal denomination of this new rose is 'Proberg'.

Among the novel characteristics possessed by this new variety which distinguishes it from its parent and all other varieties of which I am aware is its attractive pink blush flowers which are different in color from the pure white flowers of its parent. The delicate shades of pink of the petals produce what has been described as a "hand painted" look.

Asexual reproduction by propagation by budding of the new variety as performed in Narromine, NSW, Australia, shows that the foregoing and other distinguishing characteristics come true to form and are established and transmitted through succeeding propagations.

BRIEF DESCRIPTION OF ILLUSTRATION

The accompanying illustration shows typical specimens of the flowers of the new variety depicted in color as nearly true as it is reasonably possible to make the same in a color illustration of this character. Phenotypic expression may vary with light availability, environmental and cultural conditions.

DETAILED DESCRIPTION OF THE NEW VARIETY

The following is a detailed description of the variety, with color terminology in accordance with The Royal Horticultural Society Colour Chart (R.H.S.C.C.). The terminology used in color description herein refers to plate numbers in the aforementioned color chart, except where terms of common usage are employed.

Parentage:

*Mutation.*—'Iceberg'.

Class: 'Floribunda'.

The following observations are made of specimens grown outdoor in Narromine, NSW, Australia during March–April.

FLOWER

Blooming habit: Recurrent.

A. Bud:

(1) *Size.*—Medium to small.

(2) *Form.*—Pointed, ovate.

(3) *Color.*—As sepals divide, bud color is in the range of 62A, 62B and 62C, lightening toward base, with pale white to cream at base.

(4) *Sepals.*—About equal to bud length.

(5) *Peduncle.*—Length — about 2 inches. Aspect — straight to curved, some prickles. Strength — erect. Color — medium green.

B. Bloom:

(1) *Size.*—Average size when fully expanded — about 3 inches.

(2) *Borne.*—Singly and in sprays of 3 to 4 blooms.

(3) *Form.*—High centered at first, petals loosely roll outward, some outer petals quill to points.

(4) *Petalage.*—Number of petals under normal conditions — about 35.

(5) *Color.*—During first two days, inner petals at center of flower are near 62A at petal margins when bunched; as petals unfurl, varying pink tonality, near 62A–62D, becomes visible in the form of color washing into mid petal, often surrounded with near white 155D; similar coloration on petal reverse varying to light pink; light yellow, near 2D to 155D, at point of petal attachment; general tonality from a distance is shades of pink to white. Upon aging pink tones lighten.

C. Petals:

(1) *Texture.*—Thin.

(2) *Appearance.*—Inside satiny and outside satiny.

(3) *Form.*—Elliptic.

(4) *Arrangement.*—Imbricated, regularly arranged.

(5) *Petaloids in center.*—Few.

(6) *Persistance.*—Petals drop off cleanly.

(7) *Fragrance.*—Slight.

(8) *Lasting quality.*—Flowers last well on plant until petals drop.

REPRODUCTIVE ORGANS

A. Stamens, filaments, and anthers:

*Arrangement and color.*—Regularly arranged around styles.

(1) *Stamens.*—Pink.

(2) *Filaments.*—Pink.

(3) *Anthers.*—Darker pink than filaments.

(4) *Styles.*—Bunched, uneven, medium length.

(5) *Stigmas.*—Slightly yellow.

B. Hips:

*Shape.*—Urn shape.

*Size.*—Medium.

*Color.*—Green.

*Seeds.*—Seeds do not protrude.

PLANT

A. Form: Upright.

B. Growth: Vigorous, free branching.

*Height attained.*—About 2 feet.

C. Foliage: Mainly compound 5, some compound 7 leaflets.

(1) *Size.*—Medium.

(2) *Quantity.*—Abundant.

(3) *Color.*—New foliage: Upper side — Pale green with reddish edge. Underside — Reddish green. Old foliage: Upper side — Dark green. Underside — Light green.

(4) *Shape.*—Oval, oblong.

(5) *Texture.*—Upper side is semi-glossy; smooth; underside is matte.

(6) *Edge.*—Serrated.

(7) *Serration.*—Fine.

(8) *Leaf stem.*—Medium green.

(9) *Stipules.*—Medium; auricle slightly reddish.

(10) *Resistance to disease.*—Blackspot — Excellent. Mildew — Excellent. Rust — Excellent.

D. Wood:

(1) *New wood.*—Color — Reddish. Bark — smooth.

(2) *Old wood.*—Color — Medium green. Bark — smooth.

E. Thorns:

(1) *Thorns.*—Quantity (main stalk) — few. On laterals from stalk — few. Form — thin, curved downward. Length — medium. Color — tan. Position — irregular.

(2) *Prickles.*—Very few.

F. Winter hardiness: Winter hardy in Australia.

I claim:

1. A new and distinct variety of rose plant of the floribunda rose class, substantially as shown and described.

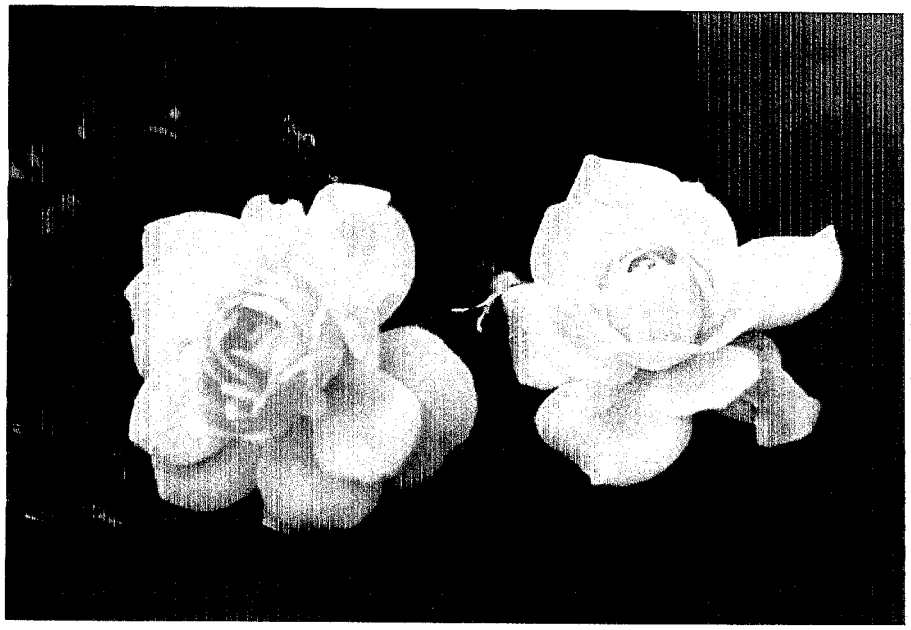

* * * * *